United States Patent
Eckmiller et al.

(10) Patent No.: US 6,970,746 B2
(45) Date of Patent: Nov. 29, 2005

(54) MICROCONTACT STRUCTURE FOR NEUROPROSTHESES FOR IMPLANTATION ON NERVE TISSUE AND METHOD THEREFOR

(75) Inventors: Rolf Eckmiller, Neuss (DE); Ralph Hünermann, Bonn (DE); Michael Becker, Bonn (DE)

(73) Assignee: Intelligent Implants GmbH, (DE)

( * ) Notice: Subject to any disclaimer, the term of this patent is extended or adjusted under 35 U.S.C. 154(b) by 185 days.

(21) Appl. No.: 09/771,283

(22) Filed: Jan. 26, 2001

(65) Prior Publication Data

US 2001/0037061 A1  Nov. 1, 2001

(30) Foreign Application Priority Data

Apr. 28, 2000 (DE) ............................... 100 20 846

(51) Int. Cl.[7] ............................................... A61N 1/05
(52) U.S. Cl. ...................... 607/116; 607/117; 607/118; 623/6.63
(58) Field of Search ............................. 600/372, 377, 600/378; 607/116–118; 623/6.63

(56) References Cited

U.S. PATENT DOCUMENTS

| 3,738,368 | A | * | 6/1973 | Avery et al. ................. 607/117 |
| 3,774,618 | A | * | 11/1973 | Avery .......................... 607/118 |
| 4,628,933 | A | | 12/1986 | Michelson |
| 4,940,065 | A | | 7/1990 | Tanagho et al. |
| 4,969,468 | A | * | 11/1990 | Byers et al. ................ 607/118 |
| 5,024,223 | A | | 6/1991 | Chow |
| 5,215,088 | A | | 6/1993 | Normann et al. |
| 5,324,322 | A | | 6/1994 | Grill, Jr. et al. |
| 5,476,494 | A | * | 12/1995 | Edell et al. ................. 607/116 |
| 5,897,583 | A | * | 4/1999 | Meyer et al. ............... 607/116 |
| 5,919,220 | A | * | 7/1999 | Stieglitz et al. ............ 600/377 |
| 6,368,349 | B1 | * | 4/2002 | Wyatt et al. ............... 623/6.63 |

FOREIGN PATENT DOCUMENTS

| DE | 44 24 753 A1 | 1/1996 |
| WO | WO 97/24156 | 10/1997 |

OTHER PUBLICATIONS

Flexible, Polyimide-Based Neural Interfaces, Thoms Stieglitz, Hansjoerg Beutel, Ralf Keller, Martin Schuettler, J.-Uwe Meyer—Fraunhofer-Institute for Biomedical Engineering, Sensore Systems/Microsystems Department Ensheimer Strasse 48, D-6686 Sankt Ingbert, Germany e-mail thomas.stieglitz@ibmt.fhg.de 8 pages date 1999.

* cited by examiner

*Primary Examiner*—Lee S. Cohen
(74) *Attorney, Agent, or Firm*—Synnestvedt Lechner & Woodbridge, LLP; Richard C. Woodbridge, Esq.; Thomas J. Onka

(57) ABSTRACT

The invention relates to a spatially adaptive, implanted microcontact structure for neuroprostheses suitable for treating functional disorders of the nervous system for the purpose of reversible anchorage on nerve tissue. The spatially adaptive microcontact structure (RAM) is characterized in particular in that an optimum contact or active connection to nerve tissue is ensured. The implanted microcontact structure comprises subareas that are movable relative to one another and that can be brought into at least two permanent desired positions relative to one another and that can be brought into a desired position during implantation for the purpose of mechanical anchorage to the nerve tissue to be contacted and can also be brought out of one desired position into another during explantation to release the anchorage.

10 Claims, 4 Drawing Sheets

MICROCONTACT STRUCTURE FOR NEUROPROSTHESES FOR IMPLANTATION ON NERVE TISSUE AND METHOD THEREFOR

THE FIELD OF THE INVENTION

The invention relates to an implantable microcontact structure for neuroprostheses for treating functional disorders of the nervous system for the purpose of reversible anchorage on nerve tissue.

BACKGROUND

Several microcontact structures for partly implanted neuroprostheses are known whose spatial microcontact arrangement is fixed by a rigid, preshaped area (see for example in U.S. Pat. No. 5,215,088).

Several microcontact structures for partially implanted neuroprostheses are known whose spatial microcontact arrangement is fixed by a partly elastic, flexible, preshaped area and that can alter as a result of the type of implant attachment and also as a result of passive matching to the tissue shape in the implant area (see for example DE-A-4424753).

The production of such a microcontact structure is disclosed (for example) in "Flexible, polyimide-based neural interfaces" Stieglitz et al, J-U. Proceedings of the Seventh International Conference on Microelectronics for Neural, Fuzzy and Bio-Inspired Systems and in IEEE Comput. Soc. 1999, pp. 112–19. Los Alamitos, Calif., USA.

A disadvantage of the known microcontact structures is that no devices and methods are provided for explantation of the microcontact structure.

Furthermore, known microcontact structures do not have mechanisms that carry out matching of the microcontact structure to the shape of the tissue to be contacted. It is therefore not possible to minimise the spacing between the microelectrodes and the neurones to be stimulated in the nerve tissue.

A further disadvantage of known microcontact structures is that they do not have the possibility of spontaneous attachment of the microcontact structure to the nerve tissue.

A disadvantage of the currently designed or available microcontact structures for epiretinal optic prostheses is that they lack features that permit incorporation in the eye in spatially compressed shape and complicated surgical techniques are therefore necessary. This difficulty will heighten in the future as the spatial dimensions of the microcontact structures become greater with an increasing number of contacts.

Furthermore, the available microcontact structures for epiretinal optic prostheses are incapable of covering the neurones of the retina that connect the region of sharpest vision with a high microcontact density since such neurones are situated in so-called parafoveal cell craters that are distinguished by a spatial crater structure.

OBJECTS OF THE INVENTION

The object of the present invention is to eliminate these disadvantages and to provide a microcontact structure that can be introduced in compressed form into the body and can be reversibly anchored on the nerve tissue.

SUMMARY OF THE INVENTION

Thus viewed from one aspect the present invention provides an implantable microcontact structure for neuroprostheses having a number of contact elements that are formed on at least one two-dimensional carrier, wherein the carrier has at least two regions that are movable relative to one another and that can assume at least two preferred positions being a basic position and an operating position.

The microcontact structure ensures a good contact or active connection to the nerve tissue since the implanted microcontact structure comprises subareas that are movable relative to one another that can be brought into at least two permanent preferred positions relative to one another. Moreover during implantation, the subareas can be brought into a desired position for the purpose of mechanical anchorage to the nerve tissue to be contacted and can (during explantation) be brought out of one desired position into another to release the anchorage.

Advantageous designs of the spatially adaptive microcontact structure and the associated methods are shown on the basis of FIGS. 1 to 4.

DESCRIPTION OF THE PREFERRED EMBODIMENTS

An advantageous device comprising a spatially adaptive microcontact structure for neuroprostheses for implantation at nerve tissue embodies the feature that the microcontact structure can be produced as a planar, two-dimensional structure using current methods for producing microcontact structures (for example on a silicon, silicon or polyimide base (see FIGS. 1–4)).

Figure 1:
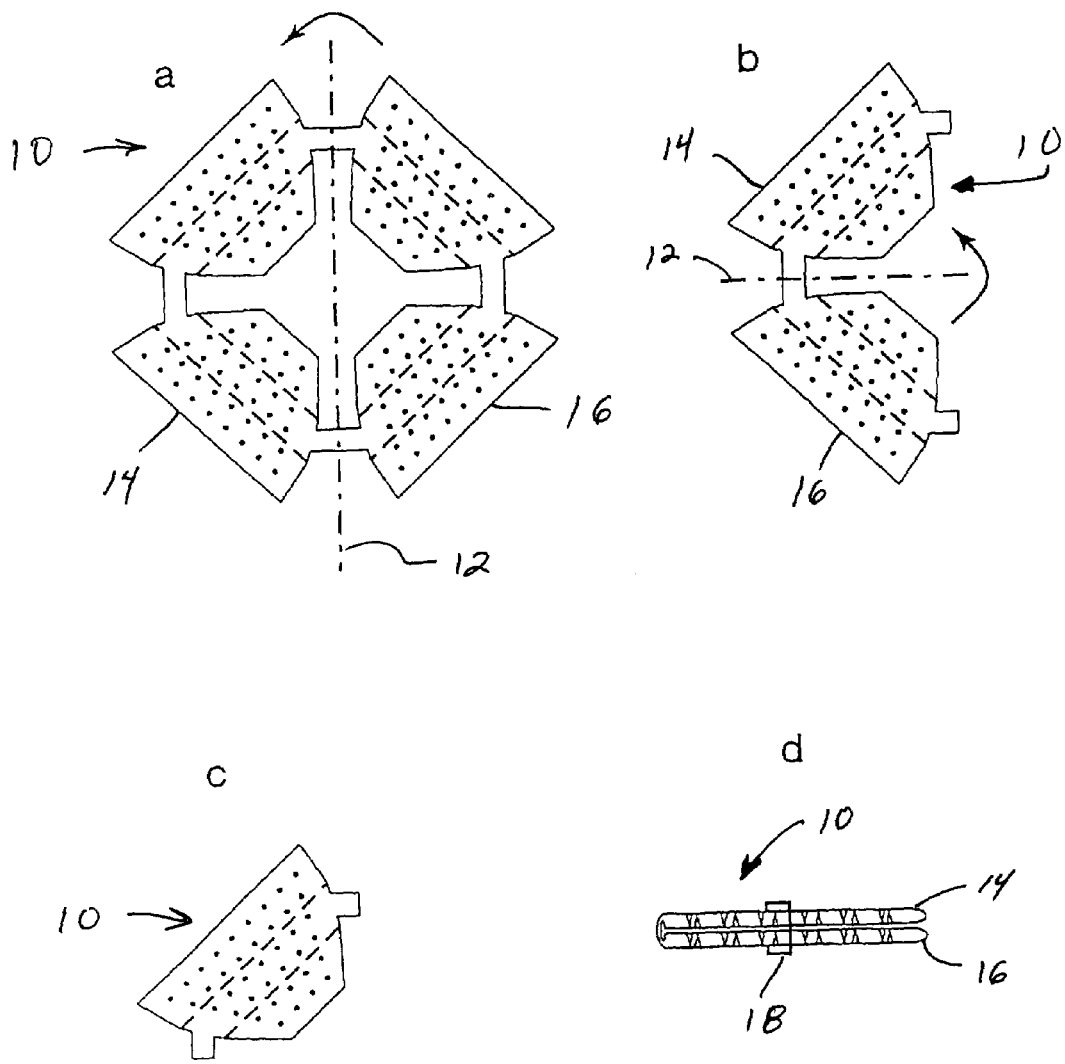
FIGS. 1a–1c illustrate the manner in which the microcontact structure can be folded.
FIG. 1d illustrates the manner in which the folded structure can be clamped in place.
Figure 2:
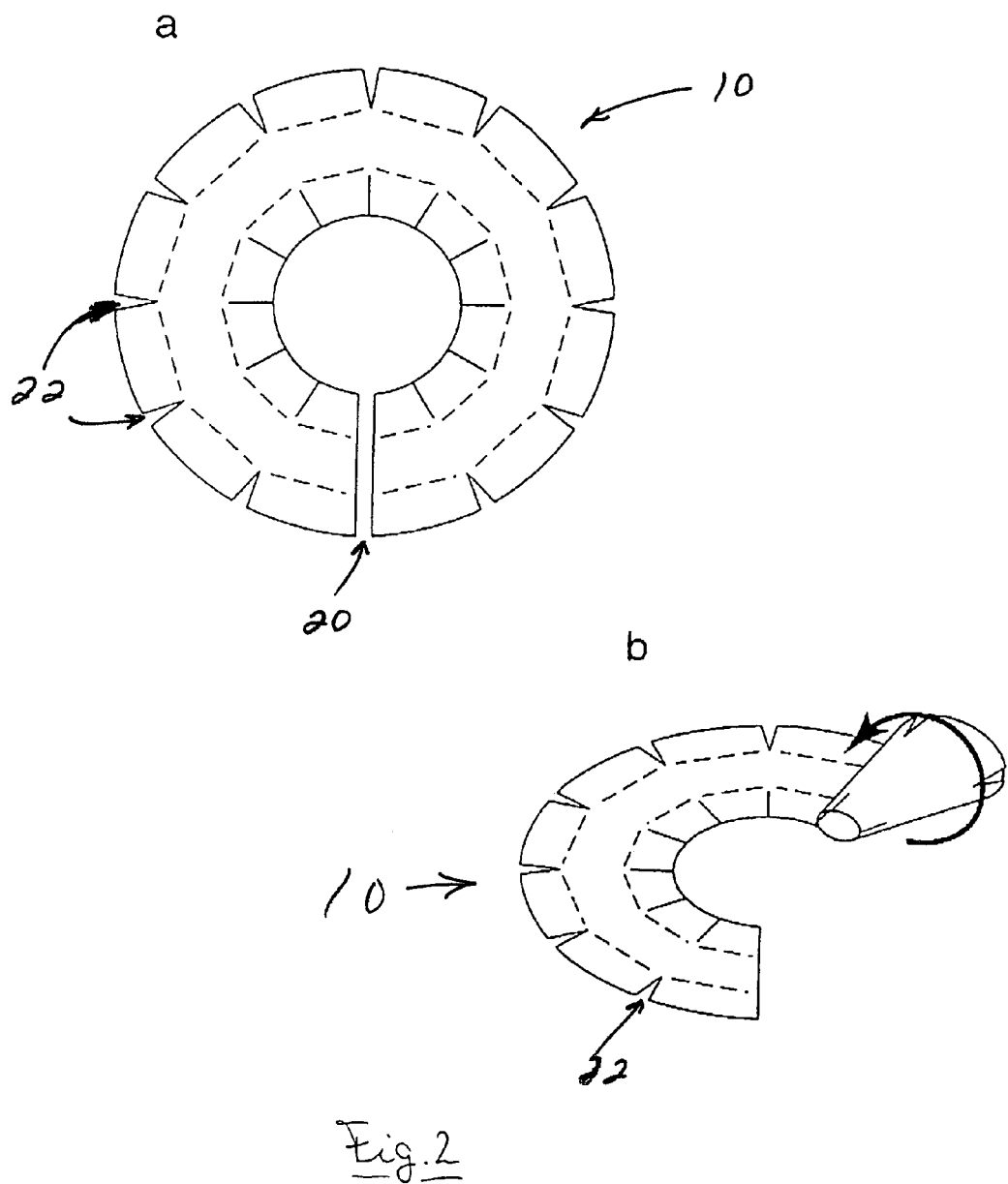
FIGS. 2a–2b illustrate the manner in which the microcontact structure can be rolled into a three dimensional object.

In the embodiments depicted in FIG. 1a and 1b a two-dimensional microcontact structure is portrayed. This structure comprises two regions, items 14 and 16, that are foldable about and axis 12. FIG. 1c depicts a simpler embodiment which depicts a microcontact structure which capable of being rolled. Accordingly, these embodiments relate to a microcontact structure that can be folded or rolled very compactly in a second step for transportation purposes in a surgical procedure. Subsequent to its delivery to the implantation point, the structure can not only be unfolded planarly in a third step but may be folded or rolled into a third dimension (See FIGS. 1–3) so that a three-dimensional structure is produced. By way of example, FIG. 2a depicts an embodiment of the invention in which the initial two-dimension microcontact structure contains a gap 20 and notches 22 which permit the structure to be rolled into a three-dimensional object.

Figure 3:
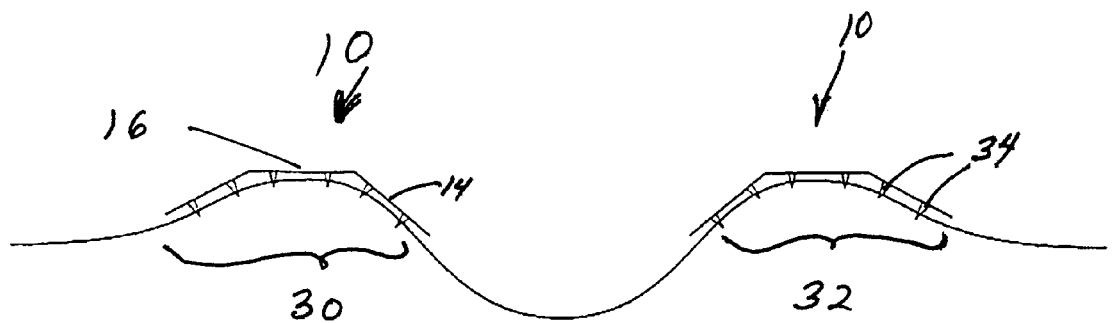
FIG. 3 illustrates the manner in which the microcontact structure can conform to the shape of a three dimensional surface.

FIG. 3 depicts an example in which the folding of regions of the structure (e.g. items 14 and 16) create three dimensional objects at the implantation sites, 30 and 32.

An advantageous design of the microcontact structure embodies the feature that it is connected to further modules of the neuroprosthesis via signal paths.

An advantageous microcontact structure embodies the feature that it is used for implantation at mammalian muscle tissue or at blood vessels or at body organs (such as for example liver, spleen, lung or kidney) and produces a unidirectional or bidirectional active connection locally at such a point.

An advantageous microcontact structure embodies the feature that on the side adjacent to the nerve tissue after implantation, are provided projecting structures (for example in the form of microelectrodes, sensors, cannulas or nails) that are essential for the mechanical anchorage of the microcontact structure. FIG. 3 depicts an example in which the folding of regions of the structure (e.g. items 14 and 16) create a three dimensional object at the implantation sites, 30 and 32.

For the purpose of conversion to a transportation position by folding, rolling or nesting of the mutually connected parts, an advantageous microcontact structure embodies the feature that segments or islands out of a preset planar basic position, spring elements (such as for example spiral springs or helical springs) and elastic elements (such as for example cushion-like microcontact structures filled with gases or liquids and enclosed with an elastic material and also for example porous, sponge-like microcontact structures) are clamped in such a way that automatic restoration of the basic position is mainly prevented by a transport lock.

An advantageous transport lock embodies the feature that the microcontact structure is held in the transportation position by a clamp that absorbs the forces or an envelope or pinning. FIG. 1d depicts an example of such a lock feature wherein the folded structure 10 is secured in this position by a clamp 18.

An advantageous operation of the transport lock embodies the feature that the transport lock is released at the implantation point by using a suitable tool so that conversion from the transportation to the basic position takes place as a controlled movement. In the case of a clamp, envelope or pin, this preferably takes place such that the forces are first absorbed by (for example) a tongue-like tool, the transport lock is then removed with a further tool and the conversion to the basic position is then controlled with the aid of the tongue-like tool.

In the case of an envelope brought about by temperature reduction or by a movement blockade produced by icing, the conversion from a locked transportation position to a basic position preferably takes place such that the mobility of its parts is restored by a controlled heat supply using a suitably shaped and controllable local heat source either as a separate tool or as an integrated element of the microcontact structure after positioning the microcontact structure at the implantation point.

In the case of an envelope brought about by temperature reduction or a movement blockade produced by icing, an advantageous microcontact structure embodies the feature that the reconversion from an operating position to a basic position is preferably brought about in that the mobility of its parts is blocked by controlled heat removal using a suitably shaped and controllable local cold source (for example, a Peltier element) as an integrated element of the microcontact structure for the purpose of re-explantation.

A further advantageous device of a spatially adaptive microcontact structure embodies the feature that the structure (which is transported locked in a folded-up state and implanted) unfolds itself on removing the lock as a result of material properties and thereby assumes a previously impressed three-dimensional structure.

A further advantageous device of a spatially adaptive microcontact structure embodies the features (as a result of the self-unfolding) that the structure assumes a shape in which it can engage with the tissue of the implantation site as a result of raised microcontacts 34 (see FIG. 3).

For the purpose of explantation, a further advantageous device of a spatially adaptive microcontact structure embodies the feature that the shortened connections on the structure can be separated and the structure brings itself back (as a result of material properties) into a planar state in which the engagements with the tissue are released.

A further advantageous device of a spatially adaptive microcontact structure embodies the feature that the structure does not require any further attachment for the purpose of positionally stable implantation as a result of the engagement.

Figure 4:
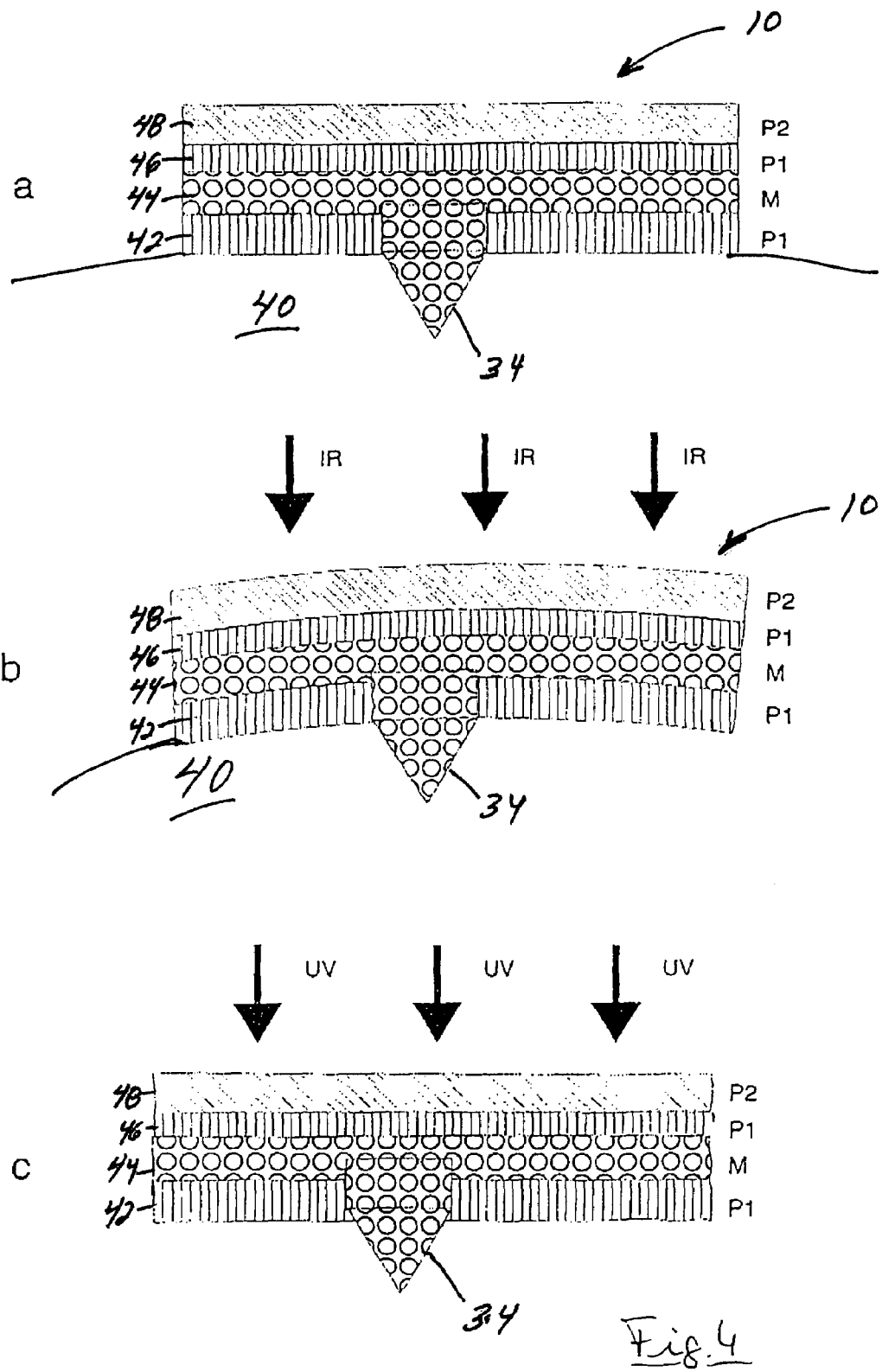
FIG. 4a is a cross-sectional illustration of the 4-layer microcontact structure in which the active connection between the microcontact structure and the nerve tissue is brought about by electrical stimulation.
FIG. 4b illustrates the manner in which the microcontact structure can be cured by infrared radiation (I.R.) so that the microcontact film is deformed at defined points by focused irradiation and matched to the nerve tissue.
FIG. 4c illustrated the deformation of the microcontact structure by focused UV treatment.

A further advantageous method embodies the feature that the microcontact structure is based on a substrate of multi-layer construction that has so-called memory properties with regard to the spatial arrangement of the microcontact structure. FIG. 4 shows a section through an advantageous 4-layer microcontact structure in which the active connection between the microcontact structure and the nerve tissue is brought about electrical stimulation.

In the embodiment depicted in FIG. 4a, the layer 42 adjacent to the nerve tissue to be stimulated 40 is composed of a polymer P1 (polyimide) and contains penetrating electrodes 34 made of a metal M such as platinum which also forms the adjoining layer 44. There follows a further layer 46 of the polymer P1 and a top layer 48 of the polymer P2 (polyurethane).

The polymer P2 has the property of a different rate of thermal expansion relative to P1. This property is utilized with an application of infrared radiation (IR) as depicted in FIG. 4b whereby a defined volume expansion is brought about by irradiation with JR light.

In this way, the microcontact structure 10 is deformed at defined points by focused irradiation and matched to the shape of the nerve tissue 40. Thus, as depicted in FIG. 4b, the structure 10 has been deformed into a slight curvature to match the curvature of the nerve tissue 40. In an additional embodiment depicted in FIG. 4c, the polymer P2 has the property of carrying out structural transitions during electromagnetic irradiation from the ultraviolet wavelength range, said transitions resulting in contraction of the material. As a result, the formation previously achieved by IR light can be compensated for, that is reversed, by means of focused UV treatment so that detachment of the microcontact structure from the nerve tissue can be performed. In this way, the re-explanation of the microcontact film is initiated.

We claim:

1. An implantable microcontact structure for neuroprostheses, said microcontact structure capable of assuming at least two desired positions for the purposes of mechanical anchorage, said desired positions comprising a basic position and an operating position, said structure comprising:

at least one contact element, formed on at least one two-dimensional carrier wherein the carrier has at least two regions that are movable relative to one another, wherein said microcontact structure has a spatial extent and wherein said spatial extent is capable of being reduced by a reducing means prior to surgical transportation to an implant point, said reducing means comprising a compacting means for compacting the regions that are movable relative to one another; and wherein said spatial extent is capable of being restored by a releasing means;

a shape modifying means wherein the desired positions of the microcontact structure can be fixed, interchanged or altered by external action before implantation, during a surgical intervention or by external signals without surgical intervention.

2. The microcontact structure according to claim 1 wherein said reducing means is selected from the group consisting of folding, nesting and rolling.

3. The microcontact structure according to claim 1 wherein said compacting places the microcontact structure in a compact state, and said microcontact structure further comprises a locking means for locking said microcontact structure in the compact state.

4. The microcontact structure according to claim 3 wherein said carrier comprises two contiguous regions and at least one junction area between said contiguous regions and wherein said microcontact structure further comprises an opening means at said at least one junction to thereby open the microcontact structure out of the compact state.

5. The microcontact structure according to claim 4 wherein said opening means is selected from the group consisting of spring forces, molecular conformation changes, pneumatic forces, hydraulic forces and electromagnetic forces.

6. An implantable microcontact structure for neuroprostheses, said microcontact structure capable of assuming at least two desired positions for the purposes of mechanical anchorage, said desired positions comprising a basic position and an operation position, said structure comprising:
   at least one contact element, and
   a shape modifying means wherein the desired position of the microcontact structure can be fixed, interchanged or altered by external action before implantation, during a surgical intervention or by external signals without surgical intervention;
   wherein the shape modifying means is utilized to attain a mechanical anchorage and takes place in a measured manner in a time-controlled sequence with respect to movement and force as a result of the external action.

7. The microcontact structure according to claim 6 wherein said shape modifying means comprises a means for responding to a signal transmitted to the microcontact structure, the signal being selected from the group consisting of electromagnetic signals, light and ultrasound.

8. An implantable microcontact structure for neuroprostheses, said microcontact structure capable of assuming at least two desired positions for the purposes of mechanical anchorage, said desired positions comprising a basic position and an operating position, said structure comprising:
   at least one contact element, and
   a shape modifying means wherein the desired positions of the microcontact structure can be fixed, interchanged or altered by external action before implantation, during a surgical intervention or by external signals without surgical intervention;
   wherein said shape modifying means is utilized to improve an electrical contact or an active connection with nerve tissue and takes place in a measured manner in a time-controlled sequence with respect to movement and force as a result of an external action.

9. The microcontact structure according to claim 8 wherein said shape modifying means comprises a means for responding to a signal transmitted to the microcontact structure, the signal being selected from the group consisting of electromagnetic signals, light and ultrasound.

10. Method for using the microcontact structure according to claim 8 in a surgical procedure, said procedure selected from the group consisting of retinal implantation for a retina implant, intracranial implantation on nerve tissue inside the skull, spinal implantation on nerve tissue of the spinal cord and its surroundings, and implantation on peripheral nerves; said method comprising the step of surgically implanting said microcontact structure.

* * * * *